(12) United States Patent
Young

(10) Patent No.: US 10,864,339 B2
(45) Date of Patent: Dec. 15, 2020

(54) AIRWAY TUBE

(71) Applicant: Indian Ocean Medical Inc., Mahe (SC)

(72) Inventor: Peter Young, Norfolk (GB)

(73) Assignee: INDIAN OCEAN MEDICAL INC., Mahe (SC)

(*) Notice: Subject to any disclaimer, the term of this patent is extended or adjusted under 35 U.S.C. 154(b) by 491 days.

(21) Appl. No.: 15/033,176

(22) PCT Filed: Oct. 23, 2014

(86) PCT No.: PCT/GB2014/053173
§ 371 (c)(1),
(2) Date: Apr. 29, 2016

(87) PCT Pub. No.: WO2015/063459
PCT Pub. Date: May 7, 2015

(65) Prior Publication Data
US 2016/0250433 A1 Sep. 1, 2016

(30) Foreign Application Priority Data
Oct. 29, 2013 (GB) .................................. 1319087.1

(51) Int. Cl.
*A61M 16/04* (2006.01)
(52) U.S. Cl.
CPC ........ *A61M 16/0493* (2014.02); *A61M 16/04* (2013.01); *A61M 16/0418* (2014.02);
(Continued)
(58) Field of Classification Search
CPC .......................................... A61M 16/04–0486
See application file for complete search history.

(56) References Cited

U.S. PATENT DOCUMENTS

| 3,606,669 A | 9/1971 | Kemble |
| 3,880,168 A * | 4/1975 | Berman ................ A61M 16/04 128/207.15 |

(Continued)

FOREIGN PATENT DOCUMENTS

| CN | 2681762 Y | 3/2005 |
| CN | 200998507 Y | 1/2008 |

(Continued)

OTHER PUBLICATIONS

International Search Report, dated Feb. 5, 2015, for International Application No. PCT/GB2014/053173.
Written Opinion of the International Searching Authority, dated Feb. 5, 2015, for International Application No. PCT/GB2014/053173.
(Continued)

*Primary Examiner* — Rachel T Sippel
(74) *Attorney, Agent, or Firm* — Morgan, Lewis & Bockins LLP

(57) ABSTRACT

An airway tube (2), an artificial airway device (1) for use in establishing an airway in a patient, and a method of manufacture are provided. The artificial airway device includes the airway tube for introduction into the patient's trachea for passage of gases to and from the patient's lungs. The airway tube defines a longitudinal axis, includes a flexible tube wall (3), and is capable of bending so as to fit into a patient's airway. The airway tube includes a distal portion (4) and a proximal portion (5), and is adapted such that all or a part of the proximal portion is relatively more resistant to bending out of the longitudinal axis than all or a part of the distal portion.

26 Claims, 4 Drawing Sheets

(52) U.S. Cl.
CPC .... *A61M 16/0434* (2013.01); *A61M 16/0463* (2013.01); *A61M 16/0465* (2013.01); *A61M 16/0497* (2013.01); *A61M 2207/10* (2013.01)

(56) References Cited

U.S. PATENT DOCUMENTS

| | | | | |
|---|---|---|---|---|
| 6,024,730 | A * | 2/2000 | Pagan | A61M 25/0054 604/264 |
| 7,918,227 | B1 * | 4/2011 | Phythyon | A61M 16/04 128/204.18 |
| 2002/0108614 | A1 * | 8/2002 | Schultz | A61M 1/0047 128/207.14 |
| 2004/0123869 | A1 * | 7/2004 | Rutter | A61M 16/0465 128/207.14 |
| 2005/0103332 | A1 | 5/2005 | Gingles et al. | |
| 2007/0144526 | A1 * | 6/2007 | Blom | A61M 16/0468 128/207.16 |
| 2008/0283052 | A1 * | 11/2008 | Young | A61M 16/04 128/200.26 |
| 2010/0163050 | A1 | 7/2010 | Hoffa | |
| 2010/0244432 | A1 * | 9/2010 | Neame | A61M 16/0465 285/21.2 |
| 2011/0061658 | A1 | 3/2011 | Koorn et al. | |
| 2015/0101611 | A1 * | 4/2015 | Wang | A61M 16/0481 128/207.15 |

FOREIGN PATENT DOCUMENTS

| | | |
|---|---|---|
| GB | 2319183 A | 5/1998 |
| JP | A59-501854 | 4/1984 |
| JP | S6049847 | 4/1985 |
| JP | H0364654 | 6/1991 |
| JP | A2013-135877 | 12/2005 |
| JP | A2011-525834 | 12/2009 |
| WO | 2009/087347 A1 | 7/2009 |
| WO | WO2010078020 | 7/2010 |
| WO | WO2012056752 | 5/2012 |

OTHER PUBLICATIONS

English Translation of Chinese Office Action dated May 2, 2017 for Chinese Patent Application No. 201480059128.3, 13 pages.
English Translation of Japanese Office Action dated Jul. 20, 2018 for Japanese Patent Application No. 2016-527413, 6 pages.
English Translation of Taiwanese Office Action dated Oct. 18, 2018 for Taiwanese Patent Application No. 103137352, 10 pages.

* cited by examiner

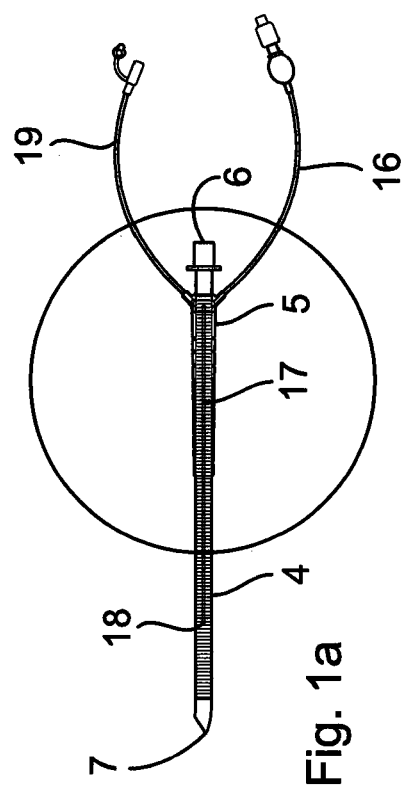
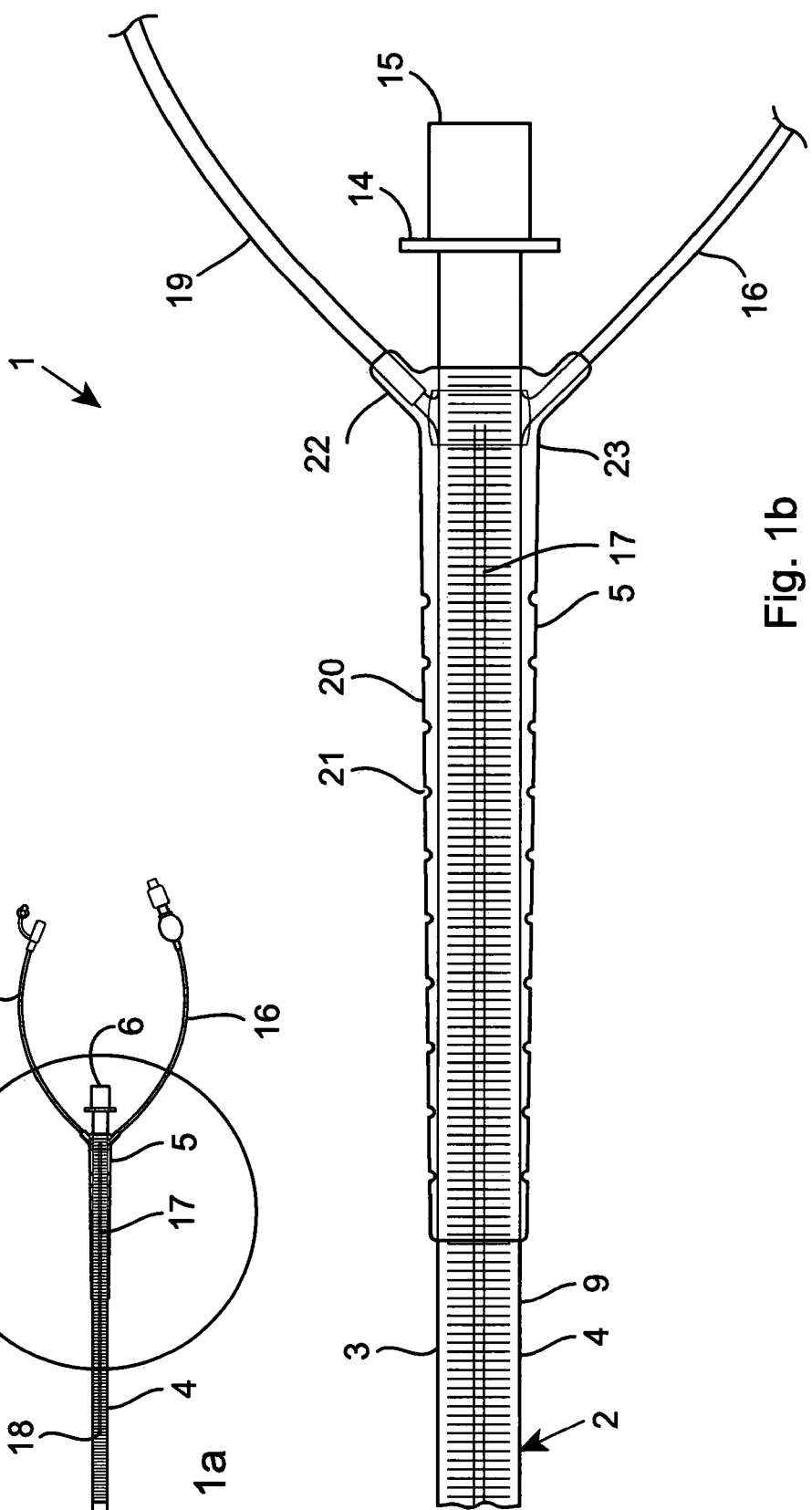
Fig. 1a
Fig. 1b

AIRWAY TUBE

CROSS-REFERENCE TO RELATED APPLICATIONS

This application is a U.S. National Stage of International Patent Application No. PCT/GB2014/053173, filed Oct. 23, 2014, which claims the benefit of United Kingdom Patent Application No. GB 1319087.1, filed Oct. 29, 2013, each of which is incorporated by reference herein in its entirety.

The invention relates to an airway tube, an artificial airway device for use in establishing an airway in a patient and in particular an endotracheal or translaryngeal tube, and a method for making a said device.

Patients kept alive by mechanical ventilators or respirators often require an artificial airway such as an endotracheal or translaryngeal tube. Such devices are very well known and have been used for many years. Over that period the art has advanced and developed to offer clinicians a wide range of devices with enhanced features and properties, sometimes at the expense of the basic requirements of ease of insertion and reliability in use. Thus, in use the tube passes from the mouth, through the oral cavity, through the pharyngeal space, past the vocal cords, through the laryngeal space and into the trachea. This pathway follows a variable number and pattern of curves depending on the nature of the patient's anatomy and as a result it is desirable, particularly for longer times of intubation, for an endotracheal tube to be very flexible so as to allow the tube to follow this pathway without causing excessive pressure or frictional damage to the tissues. This is particularly important in the portion of the pathway from the distal pharyngeal space, the arytenoid cartilages, the vocal cord and trachea as these are delicate structures. Very flexible endotracheal tubes however have a disadvantage because with patient movement and intra-oral movements of the tongue, the tube can curve and the distal tip can pull back from the trachea and even be completely removed thereby losing control of ventilation of the lungs, which is a clinical emergency. Endotracheal tubes are also known that include add on features, such as additional lumens for suction or irrigation, all of which can have an effect on the rigidity of the tube. Examples of some known devices can be found for example in GB 2 324 735A and WO 03/061747.

Additionally, patients are prone to bite into the proximal end of the endotracheal tube. A separate bite block is often required to stop biting from damaging or occluding the tube lumen. Endotracheal tubes have a narrow channel in the wall to enable the cuff at the distal ends of the tube to be inflated and many endotracheal tubes now have additional thin channels to allow secretion removal in the airway for example at a point proximal to the cuff of the tube. It is therefore desirable that the most proximal portion of the endotracheal tube is hardened to resist biting thereby protecting the lumens from damage or compression.

It is an object of the invention to seek to mitigate problems such as these.

According to the invention there is provided an airway tube for use in an artificial airway device for use in establishing an airway in a patient, the tube defining a longitudinal axis and including a flexible tube wall, the tube being capable of bending so as to fit into a patient's airway and including a distal portion and a proximal portion, characterised in that the tube is adapted such that all or a part of the proximal portion is relatively more resistant to bending out of the longitudinal axis than all or a part of the distal portion. The invention thus has the effect of stiffening the tube in the longitudinal axis so as to reduce flexibility of the tube near the mouth, oral cavity and pharyngeal space and thereby reduce the potential for movement of the tube out of the patient's airway and also to allow a higher degree of flexibility of the tube at the distal portion that is near the posterior pharyngeal space, the laryngeal inlet and the trachea in order to avoid damage to delicate tissues. As will be appreciated, the provision of the relatively more resistant proximal portion also means that some structures, such as flanges and neck plates that are presently needed for securing an endotracheal tube in place in a patient are no longer needed, as the device is integrally rigid enough to allow for direct attachment. The removal of such structures also has the advantage of allowing for improved access to the oral cavity of the patient by medical staff.

It is preferred that the proximal portion is made relatively more resistant to bending by effecting a modification to the tube wall. The said modification may be an increase in the thickness of the wall, relative to the thickness of the wall of the distal portion, and in particular may comprise an integral thickening of the wall, an additional sleeve upon the wall, or both. Providing thickening through the use of a sleeve makes manufacturing devices with varying bend characteristics much easier as the basic device structure remains the same. Where the thickening is provided by a sleeve, the sleeve may be a moulded silicone part with for example a durometer of from about 50 to about 60 Shore A.

It is preferred that the said degree of resistance to bending of the said proximal portion of the device decreases in the proximal to distal direction. This assists in correct insertion of the device, providing for a progressive bending of the tube on insertion. It is particularly preferred that the proximal portion itself comprises a proximal element of constant wall thickness and a distal element of reducing wall thickness.

Where the thickening is provided by use of a sleeve, the sleeve may comprise a through-bore of constant diameter such that it fits closely around the tube wall of an airway tube of constant diameter longitudinally. It is particularly preferred that the sleeve comprises two parts, namely a proximal part of constant outer diameter, and a transparent distal part of progressively decreasing diameter decreasing from its proximal to distal end to provide a distal taper. The said proximal part may be opaque.

Alternatively, the said modification of the tube wall may be the addition of strengthening means internally in the wall or on a surface thereof to achieve a similar progressive bending. The said strengthening means may comprise a longitudinally extending wire. The wire may extend longitudinally or as a spiral, as is known in the art, and may comprise nitinol.

It is preferred that the wall and/or the tube is resiliently deformable, such that upon deformation, including as by bending, the wall and the tube are inclined to return to their non-deformed configurations when the deforming force has been removed. As an alternative, the wall may be resiliently deformable and the tube may be fixedly deformable, such that upon deformation, the tube will remain in the shape into which it has been deformed when the deforming force has been removed. This allows the user to impart to the tube a desired shape, such as for insertion of the device, thereby removing the requirement for an introducer. The tube may comprise silicone with a hardness in the range 70 to 90 Shore A, which has been found to produce a sufficiently flexible and softly resilient distal portion to avoid tissue damage.

It is preferred that the part of the proximal portion which is relatively more resistant to bending out of the longitudinal axis is provided with one or more tape securing structure, and that the tape securing structure comprises one or more lateral groove. It is preferred that the or each groove is formed on the outer surface of the proximal portion, and it is particularly preferred that the proximal portion is provided with at least one groove on a right side and at least one groove on a left side, where the right and left sides are diametrically opposed and intended to be positioned in register with the right and left sides of the patient's anatomy when the device is in use, the arrangement being such that the or each groove provides a tape securing structure to allow for the secure attachment of tape to keep the device correctly placed in a patient.

It is preferred that, in addition to being relatively more resistant to bending out of the longitudinal axis than all or a part of the distal portion, a part of the proximal portion is adapted to be substantially more resistant to circumferential crushing than said distal portion. It is particularly preferred that said part that is resistant to circumferential crushing is disposed at an area that will be adjacent a patient's teeth when the device is in use.

According to a second aspect of the invention, there is provided an artificial airway device for establishing an airway in a patient, the device including an airway tube as set out herein above. The device may be for example an endoctracheal tube or a tracheostomy tube. The device may further include a lumen for secretion removal, and preferably the device may comprise a plurality of lumens for secretion removal and an inflation lumen for inflation of a cuff.

According to a third aspect of the invention, there is provided a method of manufacturing a tube for use in an artificial airway device, wherein the method comprises the step of optimising the resistance to bending of the tube at different points along its length according to the requirements of the anatomy for which it is intended. This is achieved by providing a tube with variable characteristics along the length. The most proximal part of the tube, which is estimated to lie adjacent to the teeth, may be hardened throughout the circumference to protect the lumens from being compressed or damaged from biting. The portion from the mouth and through the oral cavity may be stiffened in the longitudinal direction to minimise tube curling and prevent accidental or unintentional extubation. This may extend into the pharyngeal portion. The stiffening may be of a continuous nature, but it is desirable however for the stiffening to be more pronounced proximally and less so distally. This is because proximally the tissues are less prone to significant damage in the mouth and oral cavity and become more prone to significant damage more distally.

It is preferred that the step of optimising the resistance is effected through a modification to a wall of the tube, more preferably by varying the thickness of the tube wall, and most preferably by the addition of a sleeve.

According to a fourth aspect of the invention, there is provided a method of providing an artificial airway in a patient, comprising the use of an artificial airway device as hereinabove defined.

According to a fifth aspect of the invention, there is provided a method of varying the standard bending characteristics of the tube of an artificial airway device, comprising applying an external sleeve to a part or all of the tube.

The invention will further be described by way of example only, with reference to the following drawings, in which:

FIG. 1a is a plan view of a device according to the invention;

FIG. 1b is an enlarged view of area "A" in FIG. 1a;

FIG. 2a is a side view of the device of FIG. 1a;

FIG. 2b is an enlarged view of area "B" in FIG. 2a;

FIG. 4a is a part plan view of a part of the device of FIG. 1a; and

Figure 2A:
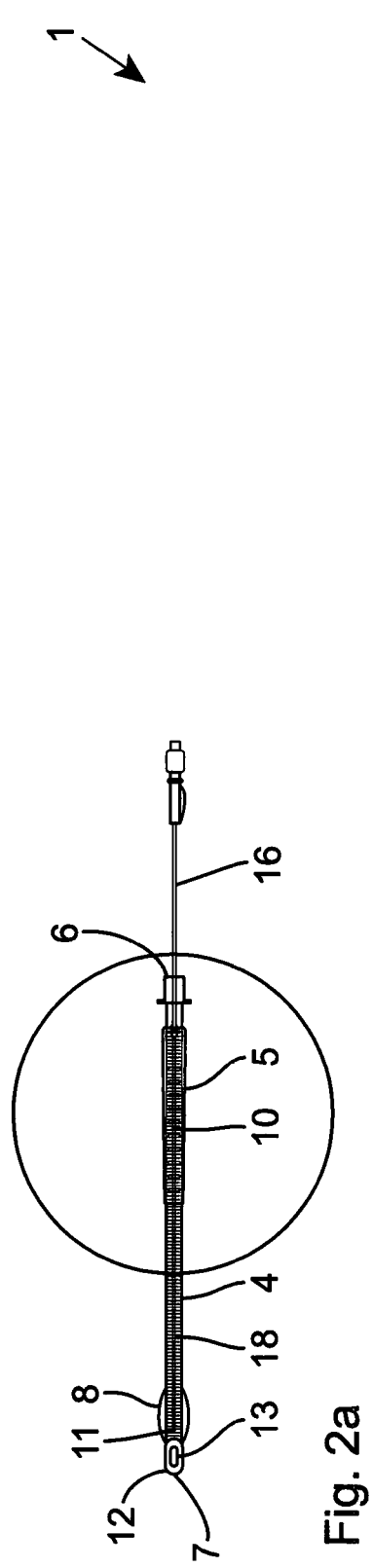

Referring to the drawings, there is illustrated an artificial airway device 1 for use in establishing an airway in a patient, the device 1 comprising a tube 2 for introduction into the patient's trachea for passage of gases to and from the patient's lungs, the tube 2 defining a longitudinal axis and including a flexible tube wall 3, the tube being capable of bending so as to fit into a patient's airway, the tube 2 including a distal portion 4 and a proximal portion 5, wherein the tube 2 is adapted such that all or a part of the proximal portion 5 is relatively more resistant to bending out of the longitudinal axis than all or a part of the distal portion 4.

In this example the invention is illustrated in use in and in the form of an endotracheal tube (or ETT), although as stated it can be applied equally well to other artificial airway devices having the same basic structure, such as tracheostomy tubes. The ETT 1 includes straight flexible hollow airway tube 2 of generally known type that extends from a proximal end 6 to a distal end 7, where the terms "proximal" and "distal" are used to denote position relative to the user of the device. Tube 2 may be made from any suitable material as is known in the art, as long as it is flexible enough to accommodate bending so as to fit into a patient's airway. In this example it is a wire-reinforced silicone of durometer about 80 Shore A. ETT 1 further includes an inflatable balloon or cuff 8 mounted near distal end 7. Balloon 8 is sealed to hollow tube 2 to form an airtight space within the balloon. ETT 1 further includes a central airway lumen 9, which extends from the proximal end 6 to the distal end 7. At its distal end 7, tube 2 is provided with tip 12, which includes opening 13, which is in fluid communication with central airway lumen 9. At its proximal end 6, tube 2 is provided with connector 14 including opening 15 which is also in fluid communication with central airway lumen 9.

Tube 2 further defines a small inflation lumen 10, which extends longitudinally through the wall 3 of tube 2. Inflation lumen 10 is provided with an access port 11 within the interior volume of balloon 8 and at its proximal end is connected to gas supply line 16. Tube 2 still further defines secretion removal lumen 17, which is a small lumen that extends longitudinally through the wall 3 of tube 2. At its distal end lumen 17 terminates in port 18 that opens through the outer surface of wall 3 proximally from balloon 8, and at its proximal end lumen 17 is connected to fluid supply line 19. As thus far described, the device 1 is of a standard and known type currently marketed under the name "Young Lotrach™ ETT".

Figure 2B:
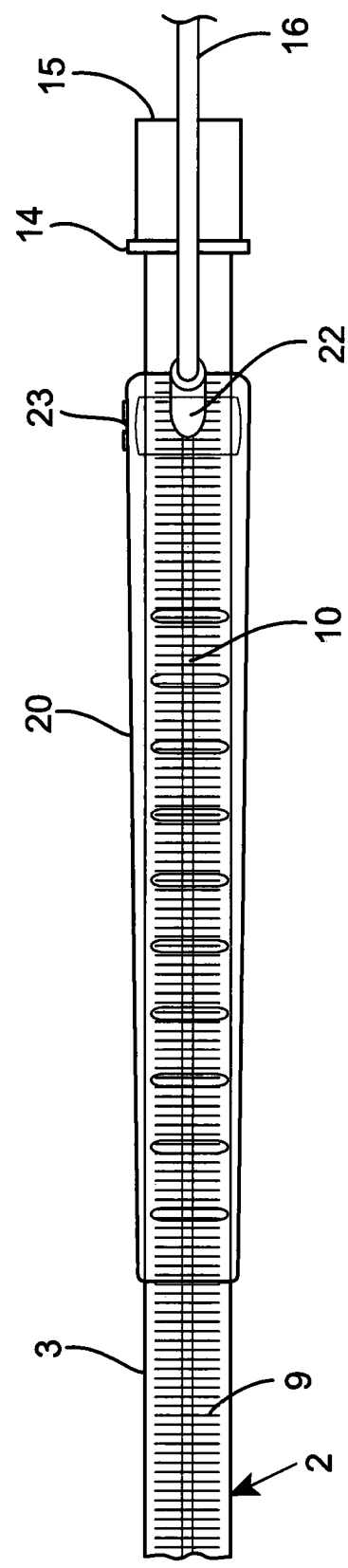
Figure 3A:
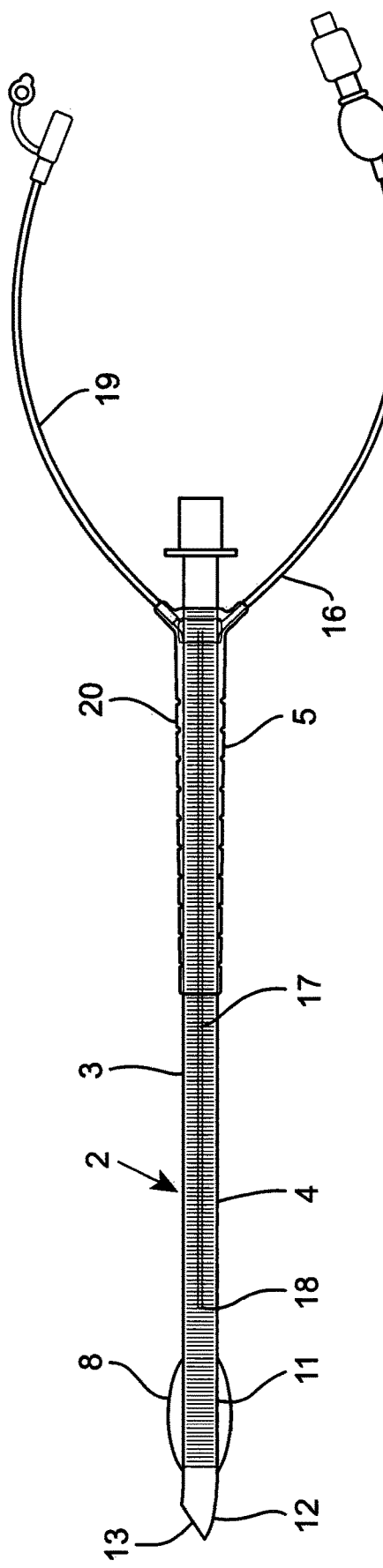
FIG. 3a is a plan view of the device of FIG. 1a in a first position.
Figure 3B:
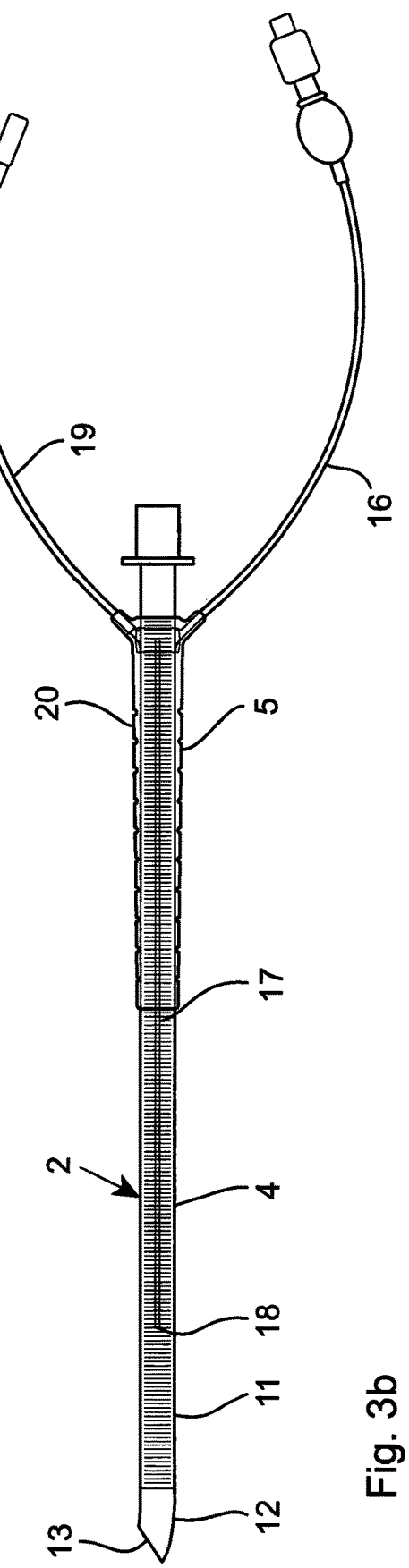
FIG. 3b is a plan view of the device of FIG. 1a in a second position.
Figure 4B:
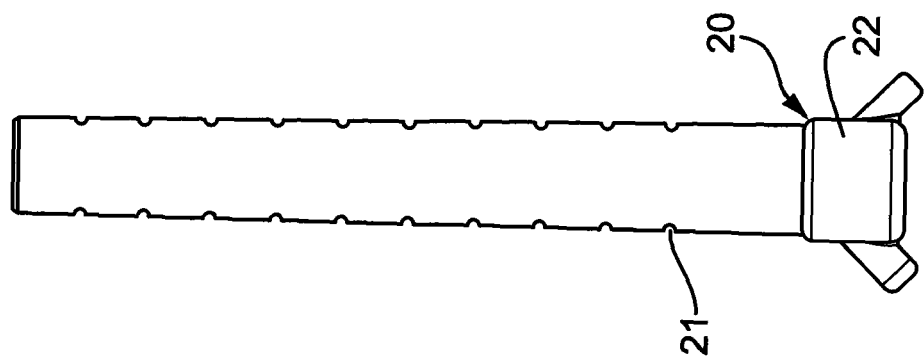
FIG. 4b is a part plan view of an alternative part for use in a device according to the invention.
Figure 4A:
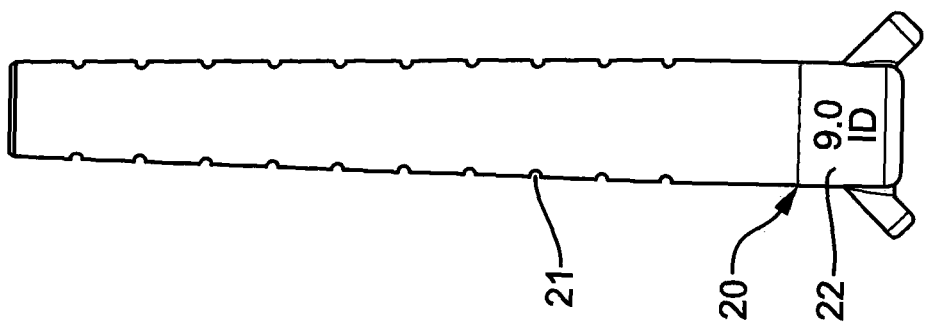

Referring now in particular to FIGS. 1b and 2b, it can be seen that tube 2 is adapted such that all or a part of its proximal portion 5 is relatively more resistant to bending out of its longitudinal axis than all or a part of the distal portion 4, by virtue of the provision of sleeve 20. As the skilled person will appreciate, sleeve 20 produces in practical effect an increase in the thickness of the proximal portion 5 of wall 3 of tube 2 relative to the thickness of the distal portion 4. The sleeve 20 is a moulded silicone part, preferably made from a silicone of durometer about 50 to 60 Shore A, clear or opaque, and is in effect a tube having a through bore of a constant internal diameter dimensioned to fit in close frictional relation over the tube 2. After a short opaque section 23 of constant diameter the external diameter of the sleeve 20 transitions to a progressively decreasing diameter section decreasing from its proximal to distal end such that the sleeve 20 can be said to distally taper. This section may preferably be transparent. Referring to FIGS. 4a and 4b, which illustrate two alternate forms of sleeve 20, it can be seen that the degree of taper can be varied. FIG. 4a illustrates a sleeve 20, which has a constant taper from proximal to distal end with no constant diameter section 23. FIG. 4b also illustrates a sleeve 20 with a constant taper, however here the degree of taper is reduced. Referring to FIGS. 1b and 2b it can be seen that the sleeve 20 is also provided with grooves 21 formed in the surface of the sleeve 20 on the left and right sides, in use, when the sleeve 20 is in correct position on the device 1. From FIG. 1b it can be seen that the left and right sides of the sleeve 20 are also each provided with an integrally moulded short tubular extension part 22 extending from the surface at approximately 45 degrees thereto in the proximal direction and dimensioned to accommodate therethrough the previously mentioned gas supply line 16 and secretion removal line 17.

In addition to providing significant clinical advantages, the invention also provides a more convenient method of manufacture because it provides a method of forming devices with widely varying characteristics very easily. As will be appreciated, it is much simpler to manufacture a single type of airway device structure and then modify it by addition of an appropriate sleeve to obtain the desired charateristics, than to have to manufacture a whole series of devices. For example, to manufacture a device 1 according to the invention, a desired taper profile is first decided upon according to the particular requirements of the anatomy of a type of patient for which a device is to be used. A sleeve 20 can be formed to impart the desired characteristics to the device with, for example, a suitably tailored bending profile and applied to a standard tube thereby varying its standard bend characteristics.

In use, the distal end 6 of ETT 1 is inserted into the mouth of a patient, through the patient's natural airway, until the distal end 6 extends into the patient's trachea. The proximal end 7 remains outside the patient. Balloon 8 is in a deflated condition while distal end 6 is being inserted into the patient. After distal end 6 has been positioned within the trachea, balloon 8 is inflated (for example by a syringe) until the outer wall of balloon 8 forms a seal with the inner mucosal lining of the trachea. Once such a seal has been established, a ventilator coupled to the connector 14 may be used to apply intermittent positive pressure ventilation to the patient. Over time, liquids such as the patient's own secretions that gather and pool can be removed by applying suction to ports 18 via suction/fluid supply line 19.

The invention claimed is:

1. An airway tube for establishing an airway in a patient, the airway tube comprising:
a tube for introduction into the patient's trachea for passage of gases to and from the patient's lungs, the tube having a longitudinal axis with a constant diameter and including a flexible tube wall, the tube being capable of bending so as to fit into the patient's airway and including a distal portion and a proximal portion, wherein the tube is adapted such that all or a part of the proximal portion is relatively more resistant to bending along the longitudinal axis relative to all or a part of the distal portion,
wherein the proximal portion of the tube comprises a ventilator connector at a proximal end of the tube, the ventilator connector having a constant wall thickness, and a sleeve distal to the ventilator connector, wherein the sleeve surrounds the tube wall and the proximal portion of the tube is resistant to bending,
wherein the sleeve comprises a through-bore of constant diameter sized and configured such that the sleeve fits closely around the tube wall radially along an entire length of the sleeve such that the sleeve is retained around the tube during use within the patient,
wherein the resistance to bending of the said proximal portion of the tube decreases in the proximal to distal direction,
wherein the sleeve comprises an increase in a thickness of the sleeve at a proximal end relative to a thickness of the sleeve at a distal end,
wherein the sleeve comprises a progressively decreasing thickness to provide a distal taper, and
wherein a wall thickness of the sleeve progressively decreases along a majority of the sleeve from the proximal end to the distal end.

2. The airway tube according to claim 1, wherein one or more of the tube and the sleeve comprises strengthening means internally in the tube wall or on a surface thereof.

3. The airway tube according to claim 2, wherein the said strengthening means comprises a wire.

4. The airway tube according to claim 1, wherein the tube wall and/or the tube is resiliently deformable, such that upon deformation, the tube wall and the tube are inclined to return to their non-deformed configurations when a deforming force has been removed.

5. The airway tube according to claim 1, wherein the tube wall is resiliently deformable and the tube is fixedly deformable, such that upon deformation, the tube will remain in the shape into which it has been deformed when a force causing the deformation has been removed.

6. The airway tube according to claim 1, wherein the tube is comprised of silicone with a hardness in a range of 70 to 90 Shore A.

7. An artificial airway device for establishing an airway in a patient, the artificial airway device comprising the airway tube of claim 1.

8. The artificial airway device according to claim 7, wherein the artificial airway device is an endotracheal tube or tracheostomy tube.

9. The artificial airway device according to claim 8, further including a lumen for secretion removal.

10. The artificial airway device according to claim 8, comprising a plurality of lumens for secretion removal and an inflation lumen for inflation of a cuff.

11. The artificial airway device according to claim 7, wherein the part of the proximal portion of the tube which is relatively more resistant to bending along the longitudinal axis is provided with one or more tape securing structures.

12. The artificial airway device according to claim 11, wherein the one or more tape securing structures comprises one or more lateral grooves.

13. The artificial airway device according to claim 7, wherein a part of the proximal portion is adapted to be substantially more resistant to circumferential crushing than said distal portion.

14. The artificial airway device according to claim 13, wherein said part that is resistant to circumferential crushing is disposed at an area that will be adjacent the patient's teeth when the artificial airway device is in use.

15. The airway tube according to claim 1, wherein a wall thickness of the sleeve progressively decreases from the proximal end to the distal end.

16. The airway tube according to claim 1, wherein a wall thickness of the sleeve progressively decreases from a portion proximate the proximal end to the distal end.

17. The airway tube according to claim 1, wherein a wall thickness of the sleeve progressively decreases constantly from a location proximate the proximal end to the distal end.

18. The airway tube according to claim 1, the sleeve includes a plurality of grooves disposed on an exterior surface of the sleeve.

19. The airway tube according to claim 1, wherein the sleeve and the tube are comprised of silicone.

20. A method of manufacturing the airway tube of claim 1, comprising:
optimizing a resistance to bending of the tube at different points along its length according to anatomical requirements for which the tube is intended.

21. The method according to claim 20, further comprising a step of providing the tube with variable characteristics along its length.

22. The method according to claim 20, wherein the step of optimizing the resistance is effected through the sleeve.

23. The method according to claim 20, wherein the step of optimizing the resistance is effected by varying the thickness of the tube wall.

24. The method according to claim 20, wherein the step of optimizing the resistance is effected by disposing the sleeve on a part of the tube, wherein the sleeve is selected such that the tube and sleeve together have a desired resistance.

25. A sleeve for use with an airway tube for establishing an airway in a patient, the sleeve comprising:
a through-bore of constant diameter sized and configured such that the sleeve fits closely and radially around a tube wall of the airway tube along an entire length of the sleeve such that the sleeve is retained around the airway tube during use within the patient, a distal portion;

and a proximal portion, wherein the sleeve is adapted such that all or a part of the proximal portion has relatively more resistance to bending along a longitudinal axis of the airway tube relative to all or a part of the distal portion, wherein the said resistance to bending of the said proximal portion decreases in the proximal to distal direction, and the sleeve comprises a proximal element having a constant wall thickness, a wall thickness of the sleeve extending distally from the proximal element having a progressively decreasing thickness to provide a distal taper, and wherein the wall thickness of the sleeve progressively decreases along a majority of the sleeve from a proximal end of the sleeve to a distal end of the sleeve.

26. An airway tube for establishing an airway in a patient, the airway tube comprising:

a tube configured for insertion into a trachea of the patient and passage of gases to and from lungs of the patient, the tube having a longitudinal axis, a generally constant diameter along the longitudinal axis, and a flexible tube wall, the tube configured to bend so as to fit into an airway of the patient and including a distal portion and a proximal portion; and a sleeve disposed over the proximal portion of the tube and including a through-bore having a generally constant diameter sized and configured such that the sleeve fits closely around the flexible tube wall radially along an entire length of the sleeve such that the sleeve is retained around the tube during use within the patient, the sleeve having a sleeve wall, a thickness of the sleeve wall progressively tapering along a majority of the entire length of the sleeve from proximate a proximal end of the sleeve to proximate a distal end of the sleeve, the sleeve being configured such that the sleeve is resistant to bending, and the resistance to bending decreasing from proximate the proximal end of the sleeve to proximate the distal end of the sleeve.

* * * * *